United States Patent [19]

Garrison

[11] Patent Number: 4,958,528

[45] Date of Patent: Sep. 25, 1990

[54] RUNOFF WATER TRAP

[76] Inventor: John M. Garrison, 3133 Waits, Ft. Worth, Tex. 76109

[21] Appl. No.: 325,050

[22] Filed: Mar. 16, 1989

Related U.S. Application Data

[63] Continuation of Ser. No. 169,220, Mar. 16, 1988, abandoned.

[51] Int. Cl.⁵ ............................................. G01N 1/12
[52] U.S. Cl. ................................................. 73/864.63
[58] Field of Search ........... 73/863.02, 863.52, 863.71, 73/864, 864.33, 864.51, 864.63, 864.64, 864.67, 864.91, 864.66, 864.02, 863.31, 863.41, 863.81, 171, 170 R

[56] References Cited

U.S. PATENT DOCUMENTS

| | | | |
|---|---|---|---|
| 914,936 | 3/1909 | Estes | 137/122 |
| 1,742,400 | 1/1930 | Larsson | 73/864.63 |
| 2,388,548 | 11/1945 | Jurs, Jr. | 73/864.66 |
| 2,675,706 | 4/1954 | Edgar | 73/863.33 |
| 2,941,405 | 6/1960 | Southwick | 73/864.63 |
| 3,625,064 | 12/1971 | Hinman, Jr. et al. | 73/863.52 |
| 3,826,144 | 7/1974 | Wessels | 73/863.31 |
| 3,830,107 | 8/1974 | Linzer et al. | 73/863.52 |
| 3,924,471 | 12/1975 | Singer | 73/864.35 |
| 4,037,477 | 7/1977 | Niskin | 73/863.01 |
| 4,089,209 | 5/1978 | Grana et al. | 73/61 R |
| 4,166,392 | 9/1979 | Farnworth | 73/863.31 |
| 4,266,429 | 5/1981 | Brovoid | 73/864.63 |
| 4,583,293 | 4/1986 | Smith | 73/864.63 |
| 4,625,574 | 12/1986 | Robbins | 73/864.91 |

*Primary Examiner*—Robert Raevis
*Attorney, Agent, or Firm*—Cushman, Darby & Cushman

[57] ABSTRACT

A device for collecting liquid samples of runoff water. The device is configured such that it does not collect any sample until a predetermined amount of runoff water has flowed. At that time, a predetermined water quantity is allowed to enter a water storage area. Once this water storage area is full, a closure occurs, and further water cannot be trapped. In the most preferred embodiment of this invention, the entire structure is formed of PVC plumbing materials. A first embodiment of the invention is adapted to be mounted vertically and uses a check valve and a float. A second embodiment of the invention is adapted for use in a runoff sewer, and collects water when the water flow is above a certain height. When the water flow becomes above a second height, a closure mechanism is activated, preventing further water from being trapped.

28 Claims, 3 Drawing Sheets

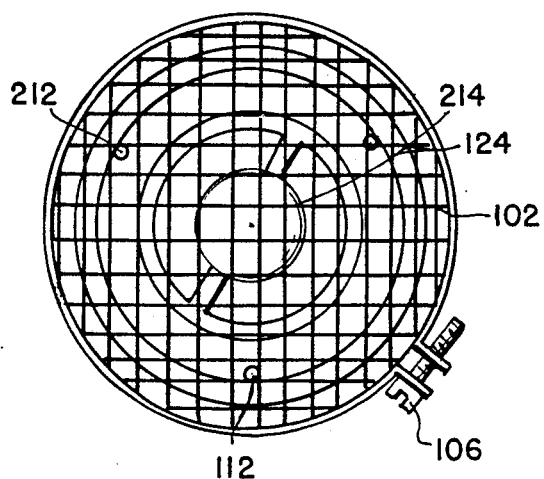
FIG. 5
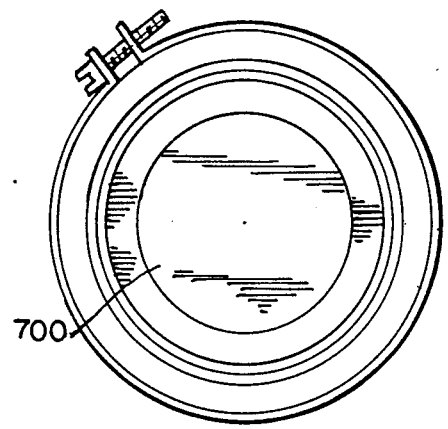
FIG. 7
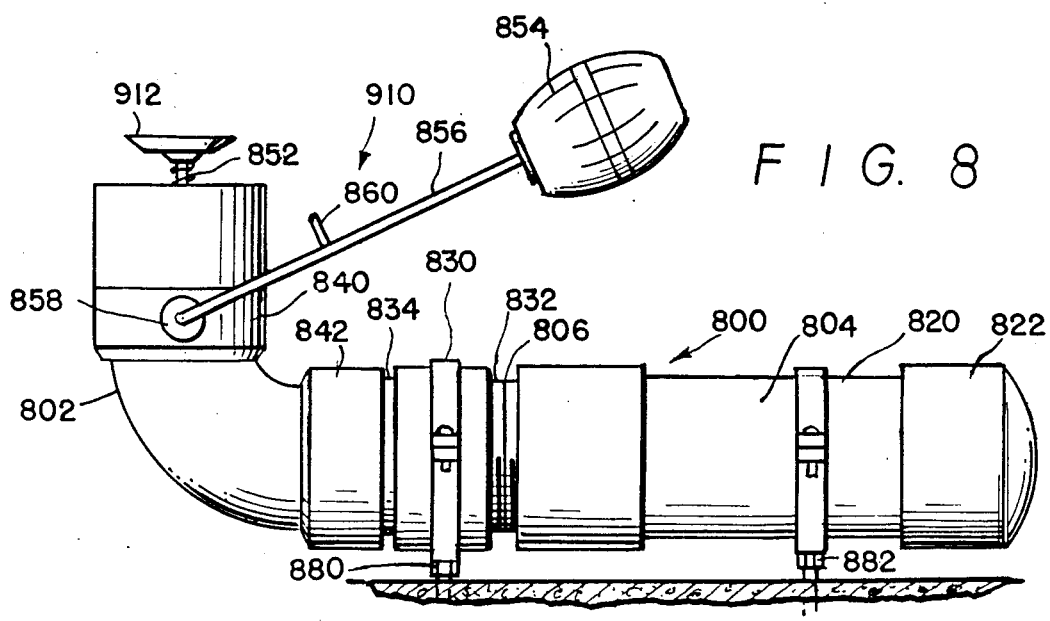
FIG. 6
FIG. 8

RUNOFF WATER TRAP

This is a continuation of Application No. 07/169,220, filed Mar. 16, 1988, which was abandoned upon the filing thereof.

FIELD OF THE INVENTION

The present invention relates to traps for collecting a quantity of runoff water.

BACKGROUND AND SUMMARY OF THE INVENTION

Since the initial advent of mechanized society, man has steadily been polluting his environment. Pollution takes different forms including water pollution, soil pollution, air pollution and the like. Moreover, such pollution exists at different levels in different areas of the country and of the world. In order to combat such pollution, it is desirable to know what various levels of pollution exist. It is also desirable to plot any large increases or decreases in pollution level.

In order to attempt to compile data on this subject, the Environmental Protection Agency (EPA) has recently proposed standards for different pollutant levels in different facets of the environment. The preferred embodiments of the present invention are specifically related to sampling the pollutant levels in municipal and industrial storm water discharges.

The pollutant level in municipal and industrial storm water discharges is a useful parameter in determining a plurality of different pollutant levels. First of all, this can determine the pollutant level in the air, as some of the pollutant level in the air will become dissolved in the rainwater that falls. In addition, there is a certain amount of silt which will also be collected. This silt will be somewhat representative of the pollutant level in and running off from the soil. In some cases it is desireable to sample a quantity of the first runoff water. In other cases it is desirable to sample the water which has already been flowing for a certain amount of time (for instance about 10 minutes) rather than merely sampling the first occurrence of water. This allows turbulence to mix all the silt and hydrocarbons into the water, in order to get a good sample. Once the sample is obtained using either technique, it is desirable to close off the sampling container such that further runoff water will not disturb the once-obtained sample. Therefore, the use of a mere bucket is clearly insufficient, as this would allow the sample, once taken to be circulated out. The sampling device must be able to accept water only after a certain running period and only a certain quantity. The prior art has never satisfactorily responded to this need.

For instance, two devices are known which have a function of sampling waste water and/or silt from storm drain runoff. One such device is made by the ISCO Company, P.0. Box 82531, Lincoln, NE 68501. ISCO model 2700 is a wastewater sampler which is electronically controlled to allow from 2 to 24 bottles to be filled during each sample. The interval between samples and the sampling amounts can be set as desired. Therefore, this is a high precision system. Unfortunately, this device is prohibitively expensive. Moreover, this system requires an electric source, either battery or AC electricity. This is highly disadvantageous in the field of the present invention, as the samples are typically taken at scattered locations in the field. It is inconvenient to have to change batteries in such a system, and even more inconvenient to have to run a source of AC electricity thereto. Therefore, this complicated system which is electrically operated is too expensive, too complicated and not portable enough for use in effectively collecting run-off and silt samples.

Moreover, this waste water sampler is suitable for use for sewage water only, and is not suitable for storm water or rainwater. The present invention is intended to be used in a plurality of different drain locations. The cost of the ISCO device would be it exorbitant if one of these devices were located in each drain.

Another known device is the LaMotte Chemical model $IS_3$ integrated sediment stream sampler. This device is made by LaMotte Chemical Products Company, P.0. Box 329, Chestertown, MD 21630. This device only collects silt and does not collect water. Therefore, this device would be unsuitable for the functions of the present invention.

Various devices have also been known in the prior art which could conceivably be adapted to trapping liquid. Therefore, these devices could possibly be used in a field such as the present invention. For example, U.S. Pat. No. 3,826,144 to Wessels teaches an apparatus for sampling liquids. The device of FIGS. 3 and 4 of that patent shows a structure which could be used for sampling liquids to block off further liquid intake after the device is filled. However, this device has a number of disadvantages.

First, no structure in this device would enable the initial water to be discarded. The device simplistically operates using a float as a closure. Therefore, the initial period of operation of the Wessels device is much like the operation of a bucket—the initial water will be captured within the liquid collection area.

Moreover, the float of Wessels is actually larger in size than the diameter of the port through which the liquid enters. This makes the assembly of the structure very difficult.

Since Wessels does not teach or suggest any valve in addition to the structure, the float merely floats to the surface to seal off the entry way to the container. Therefore, a high volume of water could force its way into the collection container, circulating out water that was already therein. This is disadvantageous as discussed above.

U.S. Pat. No. 1,742,400 to Larsson defines a structure which uses a float to open and close a valve. However, the valve and float combination of Larsson has exactly the opposite effect to that desired to sample runoff water. Specifically, the valve of Larsson is normally closed when there is no liquid in the collection container. This valve opens when the liquid in the collection container rises. There is nothing in Larsson which would provide teaching to only open the valve after a certain amount of water was in the container, to allow water to stay in the container and to keep the valve closed thereafter.

U.S. Pat. No. 2,388,548 to Jurs uses a complicated sequence of weights, pulleys and arms in order to open and close a valve. In order to close the valve on the Jurs sampling device, the device must be subjected to an external force such as a jarring force. The field of storm water collection would not provide such a jarring force to initiate the sequence.

It is therefore an object of the present invention to define such a structure which can collect runoff storm water simply, reliably and cheaply.

In order to easily sample storm water at these remote locations, it is important that the liquid collection device include only mechanical structures, so that no external source of power such as external AC power lines or a battery is necessary. It is also important that the structure be made of cheap and readily available as well as durable materials. The inventor of the present invention has found that PVC piping is ideal for such a purpose.

According to the invention in its broadest conceptual structure, a liquid collection device is defined which stores a quantity of liquid. A cavity is defined within a first structure, this cavity having the purpose of storing the quantity of liquid. This first structure has an opening at one end through which the liquid is received, and is preferably formed of a length of PVC pipe which is capped at one end. A second structure is coupled to the open end of the first structure. This second structure blocks the opening of the first structure when the first structure stores more than a predetermined quantity of liquid. Therefore, the second structure performs the function of preventing any additional liquid from being accepted once the predetermined quantity of liquid is stored. Therefore, further liquid is prevented from being cycled out.

In a preferred embodiment of the invention, the second structure is a check valve. A third structure is disposed to receive a liquid stream and selectively allows water flow into the water storing area. According to one aspect of this invention, the water flow is stored only after preventing a predetermined amount of water flow.

A first embodiment of the invention is adapted to be located in a vertical position. This first embodiment includes a liquid intake portion open at one end, defining a reservoir for storing liquid therein. A valve means communicates with the reservoir and includes a spring-biased valve. This valve maintains liquid in the reservoir until more than a predetermined amount of liquid collects therein. At that time, the weight of the liquid forces the valve to open and allows the liquid to enter a liquid storage means. Structure is also provided for maintaining the valve in the closed position once the liquid storage means is filled, so that this initial water sample can be retrieved.

The valve may also be formed with a plurality of holes therein which allow liquid to leak out slowly. A second embodiment of the invention is adapted to have the liquid collection portion located in a horizontal direction. The liquid intake portion, however, faces in a vertical direction. Moreover, the opening of the liquid intake portion is a predetermined height above the collection portion. This configuration prevents the initial water from entering the liquid collection portion. A check valve is provided in the liquid collection portion to maintain any water therein. Moreover, a closure valve is provided on the liquid intake portion which is biased into an open position, and is closed once the water level reaches a certain height. As in all the other embodiments, this embodiment is preferably formed of PVC piping.

In contrast, the device defined by the present invention can be built at the time of writing this application for one-hundredth the cost of the ISCO sampler and requires no electric source whatsoever, only using mechanical components.

BRIEF DESCRIPTION OF THE DRAWINGS

These and other advantages will be discussed with reference to the accompanying drawings, in which:

FIG. 5 shows the screen and maintaining portion in place;

FIG. 6 shows the first embodiment as it would be located within a sewer pipe;

FIG. 7 shows the check valve assembly, shown in FIG. 2, from the bottom thereof;

FIG. 8 shows a side elevation view of the second embodiment of the invention;

DETAILED DESCRIPTION OF THE PRESENTLY PREFERRED EXEMPLARY EMBODIMENTS

Figure 1:
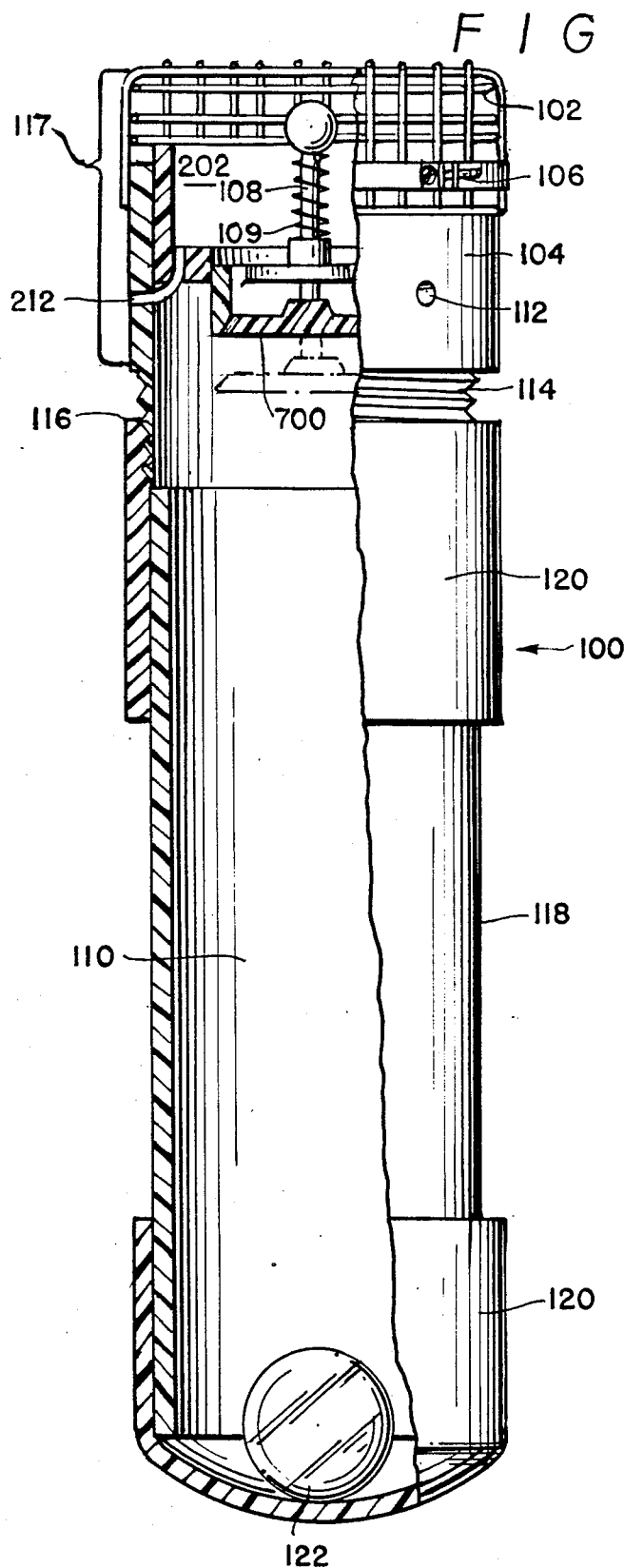
FIG. 1 shows the first embodiment of the invention in a side elevation view partially broken away.

Presently preferred embodiments will be described in detail with reference to the accompanying drawings. FIG. 1 shows a first embodiment of the present invention. This embodiment is a storm curb drain inlet device, intended for use in a vertical position. The intended use of this first embodiment is shown in FIG. 6. The device 100 is shown attached to an interior wall 602 of the storm curb drain inlet by clamps 604 and 606. Water enters storm curb drain inlet 609 in the direction shown by arrows 610 and 612. A PVC gutter 614 is installed to route the water to the inlet of storm curb drain device 100.

FIG. 1 shows this device 100 in more detail. The preferred embodiment of this invention is made of 3 inch PVC (poly-vinyl-chloride) tubing, which is readily available in most hardware stores. The top of device 100 is covered with screening 102. Screening 102 is attached to top portion 104 of the device by clamp 106. The interior beneath screening 102 includes a structure for selectively allowing water flow into the device and maintaining the water flow therein. In this embodiment, this includes structure for forming a liquid reservoir 202, and a spring biased check valve assembly 109, including spring 108, sealing the bottom of reservoir 202. Check valve 109, when open, leads into interior water storage cavity 110. The check valve assembly serves not only to block the entry of water until after a liquid stream has flowed for a time, but also to block the opening into cavity 110 when cavity 110 is storing more than a predetermined quantity of water.

A plurality of holes shown generally as 112 may be provided to allow water to escape from reservoir 202 as will be described in more detail below.

This embodiment of this invention preferably includes a threaded portion 114 which threads top portion 104 to threads 116 of sampling portion 118. Bottom portion 118 is merely a length of PVC piping with an end cap 120 formed thereupon. A float 122, preferably formed of nonporous material is also provided within internal water storage cavity 110. Screen size maintainer 124 (shown in FIGS. 4 and 5) is preferably connected over the check valve to maintain the screen in its proper position.

FIGS. 2–5 show more detailed layouts of the embodiment of FIG. 1. As described previously, bottom portion 118 of FIG. 1 can merely be a length of PVC tubing which is capped at one end with cap 120, and formed with female threads 116 at the other end. The top portion 104 selectively allows or prevents water entry or exit to the internal water storage cavity 110 which is formed within bottom portion 118. This top portion 104 constitutes an intake portion 117, and is shown in detail in FIG. 2.

Figure 2:
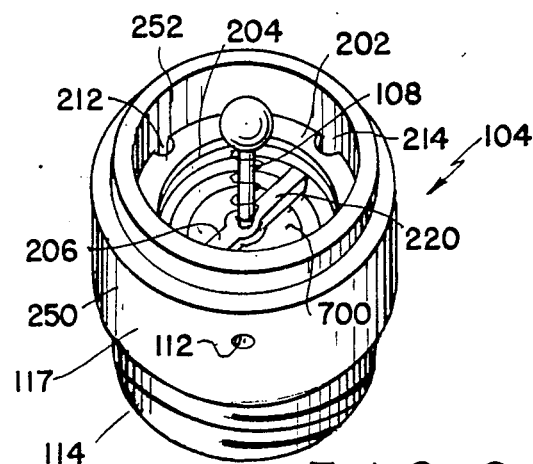
FIG. 2 shows a detailed perspective of the top portion of the first embodiment.

Intake portion 117 in FIG. 2 is threaded with male threads 114 at a bottom-most portion thereof. These male threads 114 are adapted to engage with the female threads 116 of the FIG. 1 embodiment. Male threads 114 are screwed into female threads 116, so that the device as shown in FIG. 1 can be easily assembled or disassembled.

The operative portions of intake portion 117 will now be described. Intake portion 117 is formed such that a reservoir area 202 is formed within the topmost portion thereof. In thus embodiment of this invention, this is preferably formed by taking a 3 inch threaded PVC nipple 250 which has male threads on one end and is adapted to received a 3 inch PVC pipe glued onto the other end. This end which is adapted to receive a PVC pipe then has a PVC 3 inch to some smaller size adapter 252 glued thereinto. The smaller size adapter 252 is formed with female threads 204. Check valve 206 is then screwed into these female threads 204.

This results in the reservoir area 202 being formed within the adapter 252.

Check valve 206 has a spring 108 which is chosen such that it will not compress until approximately one cup of water is located in reservoir area 202. This has the purpose of ensuring that a predetermined amount of water must fill reservoir area 202 before check valve 204 will open to allow the water to enter internal water storage cavity 110.

As described earlier, it may be desirable that the first water amounts that enter reservoir area 202 are not the water that is sampled in certain circumstances. The initially received water should not fill internal water storage cavity 110 under these circumstances. Rather, water that has flown for at least a few minutes is the water that should be sampled.

The present embodiment may optionally be provided with a means for allowing water to flow out of reservoir area 202—allowing a further time delay before enough water collects in reservoir area 202 to enable check valve 204 to open. During the time before check valve 204 opens, new water will continually circulate into and out of reservoir area 202. Moreover, a certain period of time will elapse before the check valve 204 opens. During this period of time, the water in reservoir area 202 should become similar in composition to the new water which is continually being circulated thereinto. Therefore, this means for allowing water to flow out of the reservoir performs the function of ensuring that the first water that reaches water sampler 100 is not stored. In this embodiment, the means for allowing water to flow out of reservoir area 202 is formed by holes 112, 212 and 214. These holes are drilled at a bottom-most portion of reservoir area 202, directly down into the PVC adapter 252, into which the check valve 206 is screwed. Three more holes are drilled into nipple 250. FIG. 2 shows the exit of hole 112, and the entrance of holes 212 and 214. Holes 212 and 214 are drilled such that they communicate with holes similar to 112 on the exterior of nipple 250. In addition, because of the way the check valve 206 is installed, it forms a water tight seal such that water that enters holes 112, 212 and 214 must exit the exterior holes and cannot enter internal water storage cavity 110. These holes, however, are not necessary if the first water is the water desired to be stored.

Screen 102 is also provided to ensure that sticks and other large objects do not enter the cavity 110. A stick or the like might hold check valve 206 in the open position, thereby preventing check valve 206 from closing and preventing an accurate sample from being obtained. Also, at least some of the volume of water would be displaced by such objects. Therefore, it is desirable to have screen 102 above check valve 206 to keep such extraneous material out of internal water storage cavity 110. In this embodiment, screen 102 is formed from ¼ inch chicken wire and a hose clamp of sufficient size to circumnavigate the exterior of nipple 250.

Figure 3:
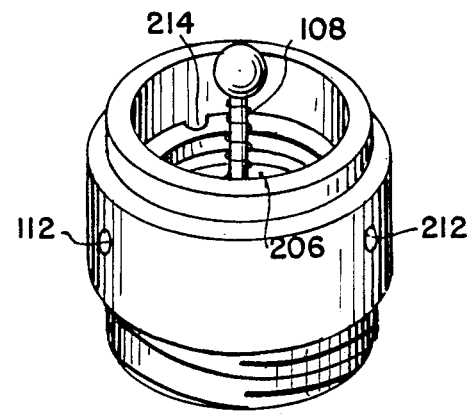
FIG. 3 shows another perspective view of this first embodiment.

FIG. 3 shows a side view of top portion 104. The top of check valve 206 can also be seen along with spring 108. Check valve 206 can be of any desired type, but in this embodiment is a back flow preventer type check valve. Water can flow from the top into internal water storage cavity 110, but water cannot flow out of internal water storage cavity 110 due to the operation of check valve 206.

Figure 4:
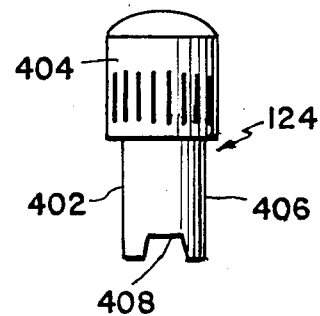
FIG. 4 shows the maintaining structure which maintains the screen of the first embodiment a predetermined distance above the intake valve.

FIG. 4 shows screen size maintainer 124. This structure includes a notched-length 402 of ½ inch PVC piping which is capped with cap 404. The bottom portion 406 includes notch 408. This notch is adapted to engage with a retaining structure 220 on the check valve. FIG. 5 shows screen size maintainer 124 in place under screen 102, and shows the entire structure from this angle.

FIG. 7 shows a bottom view of nipple area 201. The bottom flap 700 of check valve 206 can be seen in this view.

In operation of this embodiment (configured without holes 112 212 and 214) water runoff from the storm drain follows the paths of arrows 610 and 612 through PVC gutter 614 where it is coupled to the inlet portion of the device 100. Screen 102 serves to maintain any extraneous objects which may be mixed in with the water, outside of the device. Water is coupled into reservoir area 202.

At some point, the water level in reservoir area 202 becomes high enough to counteract the force of spring 108. At this time, the check valve 206 is forced open, and the water in reservoir area 202 empties into internal water storage cavity 110. This continues until the water in internal water storage cavity 110 rises high enough to bias against check valve 206. At that time, float 122 holds check valve 206 in the closed position, and further water which enters the reservoir area 202 will not enter internal water storage cavity 110.

The embodiment of FIG. 1 could also operate without float 122, as the water pressure when internal water storage cavity 110 is filled is such that check valve 206 will not be able to readily open. However, float 122 provides further assurance that the water in internal water storage cavity 110 is not circulated.

This embodiment of the invention is preferably thirteen inches high from the bottom-most portion to the beginning of the screen. The screen is advantageously located three inches above this topmost height.

FIG. 8 shows a second embodiment device 801 of the present invention. The second embodiment is adapted for use in a large run-off water area. As in the first embodiment of FIGS. 1 through 7, the embodiment of FIG. 8 uses 3 inch PVC tubing to provide a sampling device capable of inexpensively obtaining a sample.

The second embodiment includes a sampling portion 800 and an intake portion 802. The sampling portion 800 defines an internal water storage cavity 804 therewithin. The end of sampling portion 800 that communicates with intake portion 802 is labeled as portion 806. This portion is threaded such that the end can be capped and replaced in order to remove the water sample for later processing. The sampling portion 800 may be exactly the same as sampling portion 118 of the first embodiment. However, the intake portion 802 is different from intake portion 117 of the first embodiment and thus will be described in detail herewith.

Figure 9:
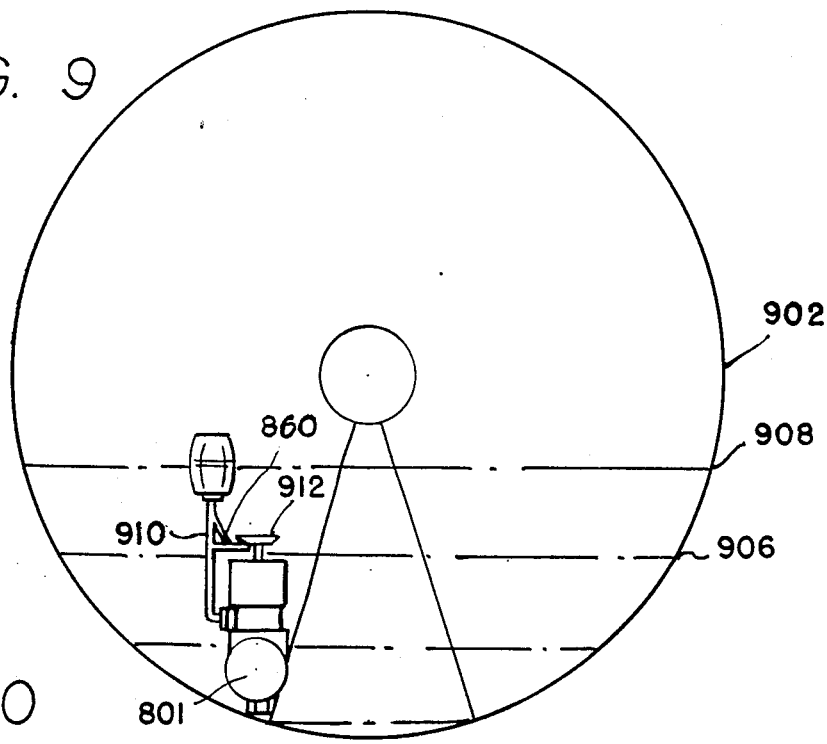
FIG. 9 shows the second embodiment in a storm drain, as it would be used.

The embodiment of FIG. 8 is intended for use in a storm sewer drain. Such drains are typically very large—of a size from 60 to 90 inches in diameter. A typical drain with this device of the second embodiment located therein is shown in FIG. 9. The device 801 is shown in storm drain 902 and operates as follows. Sample flow level 906 is defined as the top of the intake of device 801 and is 10 inches above the bottom of device 801 in this embodiment. Water lower than sample flow level 906 will not enter device 801. However, when the water level rises above sample flow level 906, water enters internal water storage cavity 804. Once this compartment is filled, no further water will be allowed to enter. As an additional safety mechanism, however, when water goes above a second level or closure flow level 908, a closure mechanism 910 is activated. This closure mechanism closes valve 912 and prevents any further water from entering intake portion 802.

The structure and operation will be described in detail with reference to FIGS. 8–12.

Sampling portion 800 includes pipe portion 820 which is capped by cap 822 at one end thereof. The other end 806 terminates with female threads.

Intake portion 802 in this embodiment is comprised of two detachable portions 830 and 840. Portion 830 includes a check valve (described later with respect to FIG. 12) therein, which can be the same as check valve 206 of the first embodiment. Portion 830 also has male threads at one end 832 thereof. The other end of portion 830 ends in PVC piping 834 that is adapted to mate with a PVC coupler.

Portion 840 begins with a PVC coupler at portion 842. Portion 840 is substantially curved at a 90° angle and opens at the top thereof. A valve 912 is located at the top thereof which is spring biased into the downward position by spring 852. Closure mechanism 910 includes in this embodiment a toilet float 854 and a rod 856. Rod 856 pivots around point 858 which is drilled through the 90° coupler 840. Rod 856 also includes valve opening abutment 860. In operation, valve opening abutment 860 is placed under valve plate 912 is open, water can open. While valve plate 912 is open, water can freely enter intake part 802 and be coupled into internal water storage cavity 804. However, when the water flow reaches the level of float 854, the force of the water causes float 854 to be moved in the direction of flow of the water. This causes valve opening abutment 860 to be disengaged from underneath valve plate 912 and the valve accordingly closes.

Figure 10:
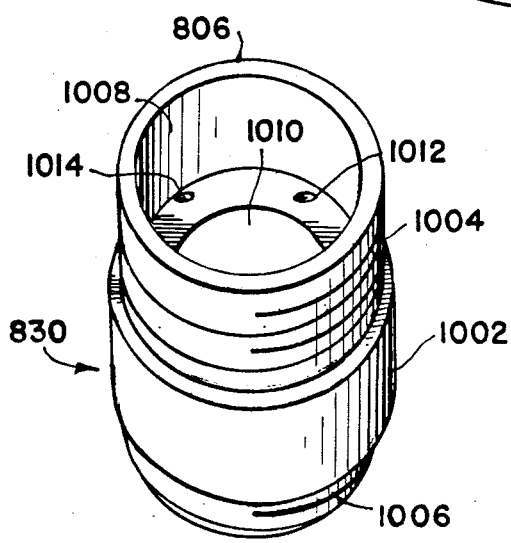
FIG. 10 shows a perspective view from the top, inlet portion of the second embodiment.
Figure 11:
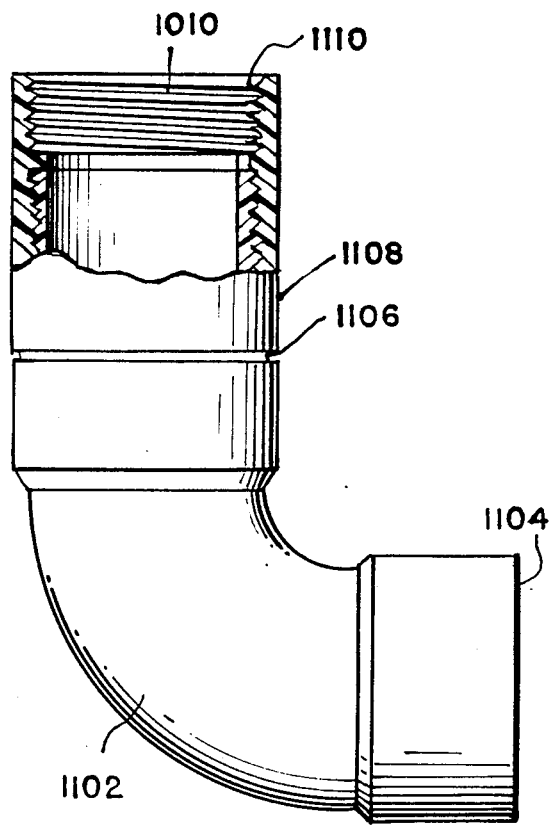
FIG. 11 shows an enlarged side elevation view of a portion of the second embodiment partially broken away.

FIG. 10 shows portion 830 of intake part 802 in detail.

Portion 830 includes a 3 inch PVC nipple 1002 which is threaded with male threads 1004 at one end 806 thereof. The other end of PVC nipple 1002 has a short length of PVC tubing 1006 glued thereinto. This length of PVC tubing 1006 glued into nipple 1002 forms a reservoir 1008 within the length of PVC tubing. Check valve 1010, which is similar to the check valve of the first embodiment is screwed into an internal portion of this reservoir. This check valve can be similar to the first embodiment in that it should not open until a sufficient amount of water pressure exists to open this valve. Relief holes 1012 and 1014 are also preferably located within this structure to enable some of the water to leak out therefrom to holes on the exterior, such as shown as hole 1051.

The length of pipe 1006 is adapted to couple with portion 840 of intake part 802 at end 1104. Portion 840 is shown in detail in FIG. 11. This portion is formed of a 3 inch PVC elbow 1102 adapted to mate with PVC pipes at both ends thereof. The one end 1104 mates with the length of piping 1006.

The other end of elbow 1102 has a short coupling length of piping 1106 and is connected to a PVC nipple 1108. This PVC nipple couples from the short length of pipe 1106 to a female thread 1110. An opening valve 1010 is screwed into the female threading 1110.

Figure 12:
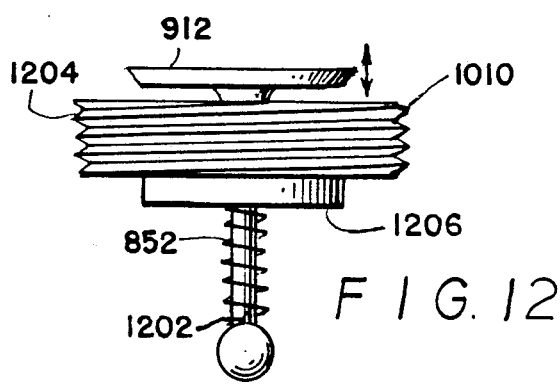
FIG. 12 shows the valve used according to the second embodiment.

Opening valve 1010 is shown in FIG. 12 in the partially open position. The valve 1010 includes valve plate 912, spring 852, rod 1202, and threaded portion 1204. The spring 852 is compressed against the bottom surface of plate 1206, tending to hold valve plate 912 into its bottom-most position.

In operation, float 854 is positioned in its vertical and uppermost, while valve opening abutment 860 is coupled under valve plate 912 to hold this valve plate into its uppermost position. The structure is secured into place using clamps 880 and 882. When water reaches level 912, water first enters intake part 802, and traverses to location 806 where the check valve 1010 is located. However, this check valve does not open until the water pressure in intake part 802 reaches a sufficiently high pressure to force this check valve open. At this time, internal water storage cavity 804 begins filling with water. This operation continues until internal water storage cavity 804 fills, at which time the back pressure on the check valve prevents further filling. However, water will continually circulate in intake portion 802. Moreover, if the water pressure got to be too intense, it could conceivable circulate water into and out of internal water storage cavity 804 by forcing open check valve 1010. Accordingly, when the water reaches a level of the float 854, it causes the valve opening abutment 860 to disengage from underneath valve plate 912. This causes valve plate 912 to close, thereby sealing off intake part 802 from further water entry.

In order to empty the embodiments of either FIGS. 1 or 8, the same basic operation can be used. In FIG. 1 the intake portion 117 can merely be unscrewed and a PVC cap used to cap portion 118. This maintains the water sample in internal water storage cavity 110. A different sampling portion 118 can then be used to screw onto intake portion 117. Emptying of the embodiment of FIG. 8 is similar. The entire structure is released from its coupling, and turned such that sampling portion 800 is substantially vertical. At this time, intake portion 802 is unscrewed and the threads on sampling portion 800 are capped with a PVC cap. This maintains the water in internal water storage cavity 804. At this time, another sampling portion can be screwed onto intake portion 802 and intake portion 802 can then be once again located.

Although only a few embodiments have been described above, those having ordinary skill in the art will readily appreciate that many modifications are possible in the preferred embodiment without materially departing from the teachings thereof. For instance, although the embodiment has been described as being formed of PVC tubing, any other king of tubing could alternately be used. In fact, the structure need not be tubing at all but could rather be rectangular piping or of any other. shape. The closure mechanisms described need not be a check valve, but can be any other mechanical structure.

Accordingly, such modifications are intended to be encompassed by the accompanying claims.

What is claimed is:

1. A liquid collection device, comprising:
   first means defining a cavity for storing a quantity of liquid, said first means formed with an opening at one end through which said liquid is received, and a closed second end, said one end including screw thread means formed thereon for allowing said first means to be connected to an disconnected from a second structure;
   second means, forming said second structure and removably coupled to said screw thread means at said one end of said first means, for automatically blocking said opening of said first means when said first means stores more than a predetermined quantity of said liquid, said second means consisting of at least one mechanical structure, and at least one of said mechanical structures is responsive to a level of liquid, said level causing said opening to be blocked; and
   third means ,adapted to be disposed to receive a liquid stream, for automatically allowing liquid flow into said first means only after preventing an initial amount of said liquid stream from entering said first means, said third means consisting of at least one mechanical structure.

2. A device as in claim 1 wherein said first means is a length of PVC piping which is capped at an end and open at said one end.

3. A device as in claim 1 wherein said second means comprises a check valve, and float means, located within said cavity of said first means ,for mechanically biasing said check valve closed when said first means becomes full.

4. A device as in claim 3 wherein said float means is formed of a non-porous material.

5. A device as in claim 1 wherein one of said mechanical structures of said third means comprises a spring coupled to said second means, means defining a liquid reservoir above said second means, and means defining a path for liquid to escape from said liquid reservoir, said spring biasing said second means into said blocking position, such that it cannot open until said reservoir has a predetermined amount of liquid therein.

6. A device as in claim 1 wherein said third means includes means defining an opening at a certain height for blocking water flow into said first means until said liquid stream achieves said certain heights.

7. A liquid collection device, comprising:
   first means defining a cavity for storing a quantity of liquid, said first means formed with an opening at one end through which said liquid is received;
   second means, coupled to said one end of said first means, for blocking said opening of said first means when said first means stores more than a predetermined quantity of said liquid, said second means consisting of at least one mechanical structure; and
   third means, disposed to receive a liquid stream, for selectively allowing liquid flow into said first means only after preventing an initial amount of said liquid stream from entering said first means, said third means consisting of at least one mechanical structure,
   wherein said third means includes means defining an opening at a certain height for blocking water flow into said first means until said liquid stream achieves said certain height;
   wherein said second means comprises a closure valve, and means for closing said closure valve when said liquid stream achieves a second predetermined height.

8. A device as in claim 7 further comprising a closure spring for biasing said closure valve into a normally closed position, and wherein said means for closing said closure valve comprises a rod for holding open said closure valve.

9. A device as in claim 8 wherein said closing means comprises:
   pivot means for pivotally supporting said rod on said third means;
   a valve opening abutment, coupled to said rod, and adapted to hold said closure valve in an open position; and
   float means, coupled to an end of said rod opposite said pivot means, for interacting with said liquid stream when said liquid stream reaches the height of said float means to displace said valve opening abutment from beneath said closure valve.

10. A device as in claim 9 wherein said float means is a toilet float.

11. A liquid collection device, comprising:
    first means defining a cavity for storing a quantity of liquid, said first means formed with an opening at one end through which said liquid is received;
    second means, coupled to said one end of said first means, for blocking said opening of said first means when said first means stores more than a predetermined quantity of said liquid, said second means consisting of at least one mechanical structure; and
    third means, disposed to receive a liquid stream and fluidly coupled to said first means through said second means, for selectively allowing liquid flow into said first means only after preventing an initial amount of said liquid stream from entering said first means, said third means consisting of at least one mechanical structure,
    wherein said third means includes means defining an opening at a certain height for blocking water flow into said first means until said liquid stream achieves said certain height,
    wherein said first means is predetermined length of PVC piping which is capped at an end thereof and open at said one end, and said third means is a PVC 90° elbow, coupled to said second means and having an end extending vertically.

12. A liquid collection apparatus adapted for use in runoff drains, comprising:
means defining a liquid storage area along a first axis, including a first closed end and a second open end adapted to receive liquid to be stored;
intake means, communicating with said storage area defining means, and having a liquid intake end disposed a predetermined vertical distance above ground level, a portion of said intake means near liquid intake end disposed along a second axis which is at a substantially right angle to said liquid storage means;
intake valve means for selectively blocking fluid from entering said liquid intake end of said intake valve means, including a closure valve, means for selectively holding said closure valve into an open position, and means for closing said intake valve means when a flow of liquid reaches a certain level,
wherein said defining means and said intake valve means are formed of PVC pipe and wherein said intake means is formed of a PVC right angle adapter; and
a spring biased check valve connected over said second open end of said storage area defining means for controlling fluid communication into said storage area defining means, said check valve opening when a predetermined amount of pressure is biased against said check valve.

13. An apparatus as in claim 12 wherein said closure valve comprises a spring biased valve which is normally biased downward to close an intake portion of said PVC right angle adapter.

14. An apparatus as in claim 13 wherein said means for biasing said closure valve comprises:
pivot means, mounted on said PVC right angle adapter;
a rod having one end pivotally mounted on said pivot means;
a valve opening abutment, coupled to said rod, and adapted to hold open said closure valve;
and wherein said closing means comprises a device at said other end of said rod for interacting with liquid flow to force said rod to move, such that said valve opening abutment becomes disengaged from said closure valve to thereby close said closure valve.

15. An apparatus as in claim 14 wherein said liquid is water.

16. A liquid collection device, comprising:
first means defining a cavity for storing a quantity of liquid, said first means formed with an opening at one end through which said liquid is received;
second means, coupled to said one end of said first means, for automatically blocking, responsive to a level of liquid in said cavity, said opening of said first means when said first means stores more than a predetermined quantity of said liquid, said second means consisting of at least one mechanical structure; and
third means, disposed to receive a liquid stream for cooperating with said second means to selectively allow liquid flow through said second means into said first means only after preventing an initial amount of said liquid stream from entering said first means, said third means consisting of at least one mechanical structure wherein said first means defines a linearly extending cavity, said second means comprises a check valve which lowers to open and raises to close, and float means, located within said cavity of said first means, for biasing against said check valve to hold it closed when said first means becomes full.

17. A device as in claim 16 wherein said float means is formed of a non-porous material.

18. A liquid collection device, comprising:
first means defining a cavity for storing a quantity of liquid, said first means formed with an opening at one end through which said liquid is received;
second means, coupled to said one ned of said first means, for automatically blocking, responsive to a level of liquid in said cavity, said opening of said first means when said first means stores more than a predetermined quantity of said liquid, said second means consisting of at least one mechanical structure; and
third means, disposed to receive a liquid stream, for cooperating with aid second means to selectively allow liquid flow through said second means into said first means only after preventing an initial amount of said liquid stream from entering said first means, said third means consisting of at least one mechanical structure wherein said at least one mechanical structure of said third means comprises a spring coupled to said second means, means defining a liquid reservoir above said second means, and means defining a path for liquid to escape from said liquid reservoir, said spring biasing said second means into a blocking position, such that it cannot open until said reservoir has a predetermined amount of water therein.

19. A liquid collection device, comprising:
a liquid collection intake portion, open at one end and defining a reservoir for storing liquid entering said one end;
a valve means, communicating with said liquid reservoir, and consisting of a plurality of mechanical structures including a valve with a spring biasing the valve, for maintaining amounts less than a predetermined amount of said liquid in said liquid reservoir when in a closed position and for automatically opening to allow liquid in said liquid reservoir to fluidly communicate with an outlet of said valve means when more than said predetermined amount of said liquid collects in said liquid reservoir;
liquid storage means, communicating with said outlet of said valve means such that liquid in aid liquid reservoir is coupled to said liquid storage means when said valve means is open, for storing a quantity of liquid; and
means for automatically maintaining said valve means in said closed position once said liquid storage means is filled.

20. A device as in claim 19 wherein said maintaining means is a float for mechanically biasing said valve into said closed position when said liquid storage means is full.

21. A device as in claim 20 wherein said float is formed of a buoyant glass ball.

22. A device as in claim 20 wherein said liquid collection intake portion is threaded at another end opposite said one end, and said liquid storage means is threaded at one end and adapted to mate with said threads on said liquid collection intake portion.

23. A device as in claim 22 wherein said liquid storage means and said liquid collection intake portion are formed of PVC piping.

24. A device as in claim 23 wherein said liquid storage means is formed by a length of PVC piping which is capped at an end and includes a threaded nipple at said one end, and wherein said liquid collection intake portion includes a threaded nipple with a length of PVC pipe glued thereinto.

25. A device as in claim 24 wherein said valve is a check valve screwed into said nipple on said liquid collection intake portion.

26. A device as in claim 22 further comprising screening means for covering said one end of said liquid reservoir.

27. A device as in claim 26 further comprising maintaining means for maintaining said screening means a predetermined distance above said one end.

28. A liquid collection device comprising:
first means defining a cavity for storing a quantity of liquid, said first means formed with an opening at one end through which said liquid is received;
second means, coupled to said one end of said first means, for mechanically blocking said opening of said first means when said first means stores more than a predetermined quantity of said liquid, and for selectively mechanically allowing liquid flow into but not out of said first means, said second means comprising of at least one mechanical structure disposed to receive a liquid stream, wherein said second means further comprises a check valve, and float means, located within said cavity of said first means, for mechanically biasing said check valve closed when said first means becomes full.

* * * * *